United States Patent [19]

Kishi et al.

[11] Patent Number: 5,191,796
[45] Date of Patent: Mar. 9, 1993

[54] ACOUSTIC-EMISSION SENSOR

[75] Inventors: Teruo Kishi, Minato; Mitsuharu Shiwa, Fujisawa; Yoshinobu Ohara, Nara; Yasuhiro Nakagami, Ikoma, all of Japan

[73] Assignee: Sekisui Kaseihin Koygo Kabushiki Kaisha, Nara, Japan

[21] Appl. No.: 744,096

[22] Filed: Aug. 9, 1991

[30] Foreign Application Priority Data

| Aug. 10, 1990 | [JP] | Japan | 2-212622 |
| Sep. 18, 1990 | [JP] | Japan | 2-249848 |
| Feb. 28, 1991 | [JP] | Japan | 3-34610 |

[51] Int. Cl.$^5$ .................. G01N 29/04; G01N 29/22
[52] U.S. Cl. .................... 73/632; 310/336; 310/358
[58] Field of Search .................. 73/587, 632; 310/336, 310/358

[56] References Cited

U.S. PATENT DOCUMENTS

| 4,122,725 | 10/1978 | Thompson | 73/632 |
| 4,371,805 | 2/1983 | Diepers et al. | 73/632 |
| 4,412,148 | 10/1983 | Klicker et al. | 310/358 |
| 4,460,841 | 7/1984 | Smith et al. | 310/358 |
| 4,927,299 | 5/1990 | Ramalingam et al. | 407/120 |

FOREIGN PATENT DOCUMENTS

| 51-20890 | 2/1976 | Japan . |
| 63-168061 | 7/1988 | Japan . |
| 2-232558 | 9/1990 | Japan . |
| 3-111755 | 5/1991 | Japan . |
| 442417 | 11/1972 | U.S.S.R. | 73/632 |
| 703480 | 2/1954 | United Kingdom | 73/632 |

OTHER PUBLICATIONS

"Acoustic Emission Testing of FRP Panel Tank", 2nd Symposium on Acoustic Emission from Reinforced Plastic (1985); Montreal, Society of Plastic Industry (SPI).
"Connectivity and Peizoelectric-Pyroelectric Composites", Mat. Res. Bull. vol. 13, pp. 525-536, 1978.
"Composites of PZT and Epoxy for Hydrostatic Transducer Application", Journal of the American Ceramic Society-Klicker et al., vol. 64, No. 1/Jan. 1981.
"Evaluation of Degradation Behavior on GFRP in Hot Water by Acoustic Emission", 3rd International Symposium on Acoustic Emission from Composite Material (1989), pp. 109-118.

Primary Examiner—Hezron E. Williams
Assistant Examiner—Rose M. Finley
Attorney, Agent, or Firm—Nikaido, Marmelstein, Murray & Oram

[57] ABSTRACT

An acoustic-emission sensor includes a composite synthetic resin-ceramic piezoelectric element which has a plurality of substantially mutually parallel columnar ceramic piezoelectric bodies. The columnar ceramic piezoelectric bodies are polarized in a longitudinal direction and are disposed in a synthetic-resin matrix. Since only longitudinal waves can be detected from among acoustic-emission waves, an intensity and variation in intensity can be detected accurately.

8 Claims, 14 Drawing Sheets

5,191,796

ACOUSTIC-EMISSION SENSOR

FIELD OF THE INVENTION

The present invention relates to an acoustic-emission sensor for detecting acoustic-emission waves.

BACKGROUND OF THE INVENTION

Acoustic emission is the phenomenon of transient elastic-wave (acoustic or ultrasonic) generation due to a rapid release of strain energy caused by a structural alteration, such as fracture or plastic distortion, in a solid material. Distortion or precursory indications of fracturing in a material are detected by measuring elastic waves (referred to hereinafter as acoustic-emission waves) which are generated due to acoustic emission as a load is applied to the material. This acoustic-emission method is in practical application in fatigue tests and materials research.

An ultrasonic receiver element made of a piezoelectric element is used in an acoustic-emission sensor which detects acoustic-emission waves. A balanced type acoustic-emission sensor is disclosed in the Japanese Laid-Open Publication No. 20890 (1976) (Tokukai-sho 51-20890). In the balanced type acoustic-emission sensor, a contacting area of the piezoelectric element with a test material is provided with electrical insulating material and two piezoelectric elements are arranged in a two-step configuration. This results in a reduction in electrical noise picked up by the sensor and a reduced occurrence of phase differences between the acoustic-emission waves detected by each of the piezoelectric elements.

When ultrasonic waves are propagated through a material, longitudinal waves are transmitted faster than transverse waves. Accordingly, if only the longitudinal waves are detected from among the acoustic-emission waves, a magnitude of acoustic emission from an acoustic-emission wave generating source can be detected accurately, without any interference from the transverse waves which reach the acoustic-emission sensor after the longitudinal waves.

However, with the conventional arrangement, both the longitudinal waves and the transverse waves are detected. Consequently, problems exist such as inaccurate detection of distortion or of precursory indications of fracturing in a material.

SUMMARY OF THE INVENTION

An object of the present invention is to provide an acoustic-emission sensor which detects only longitudinal waves from among acoustic-emission waves.

In order to achieve the above object, an acoustic-emission sensor of the present invention is characterized in comprising a composite synthetic resin-ceramic piezoelectric element in which columnar ceramic piezoelectric bodies are polarized in a longitudinal direction thereof and are arranged in a synthetic-resin matrix.

With the above arrangement, a potential difference develops between two end-faces of the composite synthetic resin-ceramic piezoelectric element only with respect to longitudinal waves among the acoustic-emission waves. This is because the columnar ceramic piezoelectric bodies have been polarized in the longitudinal direction. Accordingly, the acoustic-emission sensor detects only the longitudinal waves.

For a fuller understanding of the nature and advantages of the invention, reference should be made to the ensuing detailed description taken in conjunction with the accompanying drawings.

BRIEF DESCRIPTION OF THE DRAWINGS

FIG. 1 shows a longitudinal sectional view of an acoustic-emission sensor.

FIG. 2 shows a perspective view of a composite synthetic resin-ceramic piezoelectric element.

FIG. 3 shows a wave-form of pseudo acoustic-emission waves.

FIG. 5 shows a longitudinal sectional view of an acoustic-emission sensor.

FIG. 6 shows a perspective view of a composite synthetic resin-ceramic piezoelectric element.

FIG. 7 shows a longitudinal sectional view of an acoustic-emission sensor.

FIG. 8 shows a perspective view of a composite synthetic resin-ceramic piezoelectric element.

FIG. 9 is a graph showing frequency-dependence of an output level of an acoustic-emission sensor.

FIG. 10 is a graph showing frequency-dependence of an output impedance of an acoustic-emission sensor.

FIG. 11 shows a longitudinal sectional view of an acoustic-emission sensor.

FIG. 12 shows a transverse sectional view of a composite synthetic resin-ceramic piezoelectric element.

FIG. 13 shows a side view of an acoustic-emission sensor.

FIG. 14 shows a transverse sectional view of a composite synthetic resin-ceramic piezoelectric element.

FIG. 15 shows a transverse sectional view of a composite synthetic resin-ceramic piezoelectric element.

FIG. 16 shows a transverse sectional view of a composite synthetic resin-ceramic piezoelectric element.

FIG. 17 shows a transverse sectional view of a composite synthetic resin-ceramic piezoelectric element.

FIG. 18 shows a longitudinal sectional view of a composite synthetic resin-ceramic piezoelectric element.

FIG. 19 shows a transverse sectional view of a composite synthetic resin-ceramic piezoelectric element.

FIG. 20 is a block diagram of an instrument for measuring frequency characteristics of an acoustic-emission sensor.

FIG. 21 is a graph showing frequency-dependence of an output-voltage ratio.

FIG. 22 is a graph showing frequency-dependence of an output-voltage ratio.

FIG. 23 shows a longitudinal sectional view of an acoustic-emission sensor.

FIG. 24 is a block diagram of an instrument for measuring frequency characteristics of an acoustic-emission sensor.

FIG. 25 is a graph showing frequency-dependence of an output-voltage ratio.

DESCRIPTION OF THE EMBODIMENTS

A first embodiment of the present invention is described hereinbelow, referring to FIGS. 1 to 3.

Figure 1:
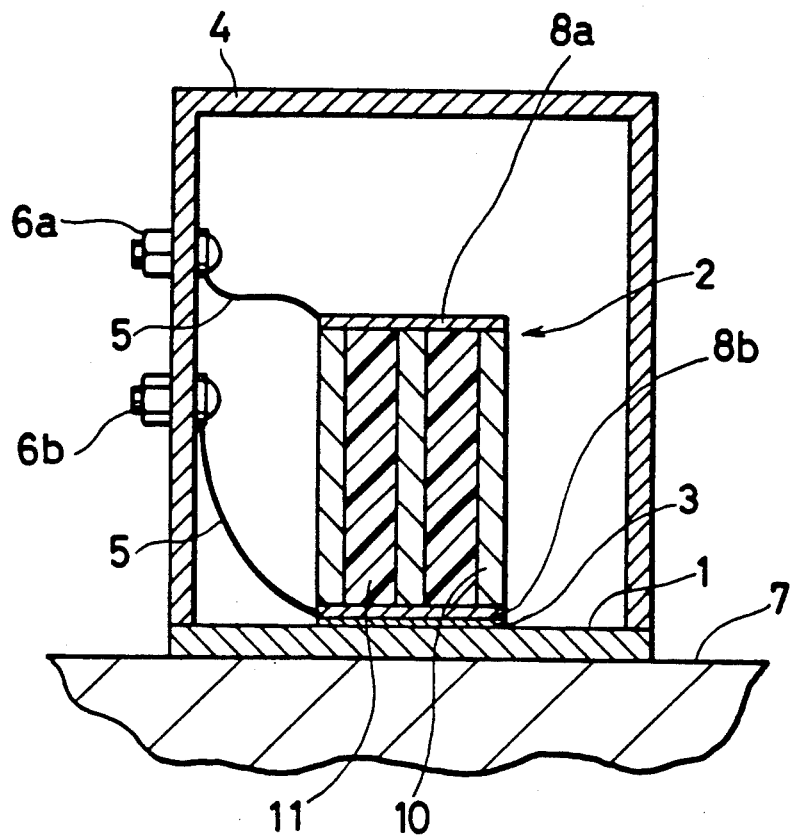
FIGS. 1 to 3 show a first embodiment of the present invention.

As shown in FIG. 1, the acoustic-emission sensor of the present embodiment comprises a receiving plate 1 for receiving acoustic-emission waves generated by a test material 7, a composite synthetic resin-ceramic piezoelectric element 2 provided above the receiving plate 1 for converting the acoustic-emission waves into electric signals, a case 4 for housing the composite synthetic resin-ceramic piezoelectric element 2, and a pair of lug terminals 6a and 6b for releasing the electric signals.

Figure 2:
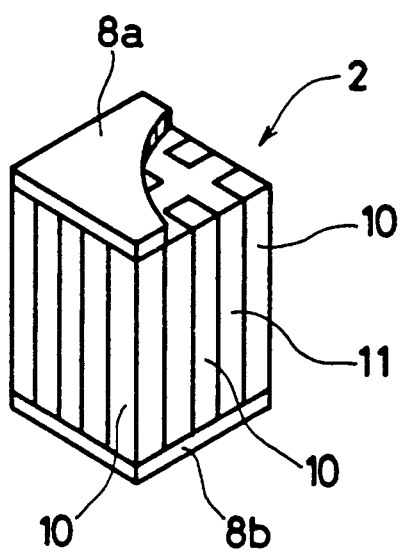

As shown in FIG. 2, the composite synthetic resin-ceramic piezoelectric element 2 comprises columnar ceramic piezoelectric bodies 10 arranged in rows to be substantially mutually parallel in a longitudinal direction thereof (an up-down direction in FIG. 1) in a synthetic-resin matrix 11. The columnar ceramic piezoelectric bodies 10 are quadrangular in a sectional view. Electrodes 8a and 8b are provided on upper and lower end-faces respectively of the columnar ceramic piezoelectric bodies 10. In each of the columnar ceramic piezoelectric bodies 10 there are piezoelectric crystal grains. A crystal axis of each of the piezoelectric crystal grains is oriented and polarized in the longitudinal direction.

The composite synthetic resin-ceramic piezoelectric element 2 is fixed to the receiving plate 1 by an adhesive layer 3. The electrodes 8a and 8b are connected respectively to the lug terminals 6a and 6b by lead wires 5 (see FIG. 1).

With the above arrangement, acoustic-emission waves generated inside the test material 7 are transmitted to the composite synthetic resin-ceramic piezoelectric element 2 via the receiving plate 1 which is in contact with a surface of the test material 7. The acoustic-emission waves are converted into electric signals by the composite synthetic resin-ceramic piezoelectric element 2 due to the piezoelectric effect. The electric signals are released through the lug terminals 6a and 6b.

In the composite synthetic resin-ceramic piezoelectric element 2 of the present embodiment, positive and negative charges develop on the two end-faces of each of the columnar ceramic piezoelectric bodies 10 only when compression and tension of the composite synthetic resin-ceramic piezoelectric element 2 take place in the longitudinal direction. This is because the piezoelectric crystal grains whose crystal axes are oriented and polarized in the longitudinal direction are provided the columnar ceramic piezoelectric bodies 10. Charges do not develop if compression and tension of the composite synthetic resin-ceramic piezoelectric element 2 take place in any other direction, such as a direction orthogonal to the longitudinal direction. Consequently, only longitudinal waves are detected from among the acoustic-emission waves which are generated inside the test material 7 and which reach the receiving plate 1.

Transverse and longitudinal waves are generated due to acoustic emission whose sources differ spatiotemporally. Consequently, when longitudinal waves and transverse waves are generated due to acoustic emission, respective propagation speeds of the longitudinal waves and the transverse waves are different. However, even if the longitudinal and the transverse waves reach the acoustic-emission sensor simultaneously due to a difference in the respective propagation speeds, only the longitudinal waves are detected. As a result, intensity and variation in intensity of acoustic emission occurring within the test material 7 can be accurately detected.

When a constant compression and tension are applied in a longitudinal direction to the composite synthetic resin-ceramic piezoelectric element 2, a potential difference that develops between the electrode 8a and the electrode 8b depends only on the shape and material of the columnar ceramic piezoelectric bodies 10. Therefore, if ultrasonic waves whose intensity is known are applied and a potential difference that develops at that time is measured, the relation between the intensity of the ultrasonic waves and the potential difference can be found. Using this relationship, an intensity of acoustic-emission waves can be found by measuring the potential difference that develops when the acoustic-emission waves are received.

Further, the columnar ceramic piezoelectric bodies 10 need not necessarily be quadrangular in the sectional view; they may equally be hexagonal shaped. Moreover, they need not be polygonal; they may equally be circular or elliptical in the sectional view.

The columnar ceramic piezoelectric bodies 10 should preferably be made of material such as sintered barium titanate, sintered lead titanate or sintered PZT (lead zirconate titanate) since this increases sensitivity of acoustic-emission wave detection. However, any other material may equally be used as long as it exhibits the piezoelectric effect and as long as it is polarized in the longitudinal direction. Regarding the dimensions of the columnar ceramic piezoelectric bodies 10, a ratio of a length (in the longitudinal direction) to a side of a lower face of each of the columnar ceramic piezoelectric bodies 10 should preferably be over 2 since this increases sensitivity of acoustic-emission wave detection. It is even better if the ratio lies in the range 2–6. Also, the modulus of elasticity of the columnar ceramic piezoelectric bodies 10 should preferably be more than 6000 kgf/mm$^2$ since this too increases sensitivity of acoustic-emission wave detection.

Synthetic resin used in the synthetic-resin matrix 11 is bonded to the columnar ceramic piezoelectric bodies 10 and may be made of any material as long as the synthetic resin and the columnar ceramic piezoelectric bodies 10 can be mutually integrated. Specifically, materials such as silicon rubber, urethane rubber, butadiene rubber, nitrile rubber, ethylene-propylene rubber, chlorophrene rubber, fluororubber, ethylene acrylate rubber, polyester elastometric rubber, epichlorohydrin rubber, acrylic rubber, or chlorinated ethylene rubber may be used. The use of silicon rubber, urethane rubber or butadiene rubber is particularly preferable because these materials speedily attenuate any transverse vibrations generated in the columnar ceramic piezoelectric bodies 10. Further, the modulus of elasticity of the synthetic resin should be 1–50 kgf/mm$^2$ since an acoustic impedance of the acoustic-emission sensor and an acoustic impedance of the test material 7 (FIG. 1) will then match.

In the composite synthetic resin-ceramic piezoelectric element 2, a ratio of a total volume capacity of the columnar ceramic piezoelectric bodies 10 to a volume capacity of the synthetic-resin matrix 11 should preferably be in the range of 8/92 to 40/60 since this increases sensitivity of acoustic-emission wave detection.

The use of the acoustic-emission sensor of the present embodiment is not limited to the detection of acoustic-emission waves. It may also be used to detect any elastic waves which are propagated through any solid, liquid or gaseous medium. Conversely, elastic waves may be generated by applying an a.c. voltage from an external source between the electrodes 8a and 8b.

A manufacturing method of a composite urethane rubber-PZT piezoelectric element as a specific example of the composite synthetic resin-ceramic piezoelectric element 2 is described hereinbelow. Performance of an acoustic-emission sensor using this composite urethane rubber-PZT piezoelectric element is also described.

A fine-processed PZT material is achieved by the following process Circular-columnar (diameter 10 mm; length 10 mm) polarized sintered PZT (produced by Honda Electronics Company; model number HC-50GS) is used as material for the columnar ceramic piezoelectric bodies 10. Five 5 mm-deep straight-line grooves are formed on one end-face of the sintered PZT at intervals of 1.5 mm. Orthogonal to these are formed another set of five 5 mm-deep straight-line grooves, also at 1.5 mm intervals. Accordingly, 32 square columns are formed in a regular, checkerboard pattern on a 5 mm-thick circular PZT plate section. Each of the square columns is 1 mm $\times$ 1 mm $\times$ 5 mm in dimension. An ultrasonic-wave processing device (produced by Japan Electronic Industry Company; model UM-5000DA) provided with a machine shop tool made from structural carbon steel (JIS: S45C) is used in the above process.

The composite urethane rubber-PZT material is manufactured as described hereinbelow. The fine-processed PZT material achieved as described above is inserted into a silicon forming die. Then, electrical insulating urethane rubber (produced by Sanyurejin Company; product name SU-1053-9; hardness 52; black), which serves as material for the synthetic-resin matrix 11, is charged into the silicon forming die and left at room temperature for one day. The urethane rubber is then hardened by carrying out hardening processing at 60° C. for five hours in an oven. The composite urethane rubber-PZT material thereby formed is then removed from the forming die.

Next, the circular PZT plate section of the composite urethane rubber-PZT material is cut away by a diamond blade (produced by Maruto Company; crystal cutter) to obtain a composite urethane rubber-PZT piezoelectric body comprising the 32 square columns which are 1 mm $\times$ 1 mm $\times$ 4 mm in dimension. The square columns are made from PZT and are formed in a regular, checkerboard pattern in the urethane rubber matrix. Both end-faces are then polished with sandpaper.

Silver paste (produced by Deguza Company; product name DEMETRON 6290-0275) is applied on one of the end-faces of the composite urethane rubber-PZT body and on a side-face close to the other of the end-faces. A silver electrode is then formed as the electrode 8a by performing baking processing for 30 minutes at 120° C. Using the sputtering method, a gold electrode is formed as the electrode 8b on the other end-face which is a lower face of the composite urethane rubber-PZT body. A thin alumina diaphragm (Mitsubishi Materials Corp.; model number MAB-L201K-10) is adhered to a surface of the gold electrode using an adhesive. The alumina diaphragm is 0.2 mm thick and serves as the receiving plate 1. An acoustic-emission sensor comprising a composite urethane rubber-PZT piezoelectric element is then achieved by soldering the lead wires 5 respectively on an upper-face of the silver electrode and on a side-face of the gold electrode.

The performance of the acoustic-emission sensor was tested by generating pseudo acoustic-emission waves by pressing down and breaking a pencil core of diameter 0.5 mm (hardness H) and detecting the pseudo acoustic-emission waves by the acoustic-emission sensor.

An aluminum plate (400 mm $\times$ 400 mm $\times$ 60 mm) was used as a transmission medium for the pseudo acoustic-emission waves. The pseudo acoustic-emission waves were detected by the acoustic-emission sensor through the aluminum plate. A digital storage oscilloscope (Hewlett-Packard Company; Model HP-54201D; printer: 6 bit/200 MHz) was used for detecting and recording converted electric signals. The acoustic-emission sensor and the digital storage oscilloscope were connected by a one-meter long coaxial cable (corresponding to 5D2V).

Figure 3:
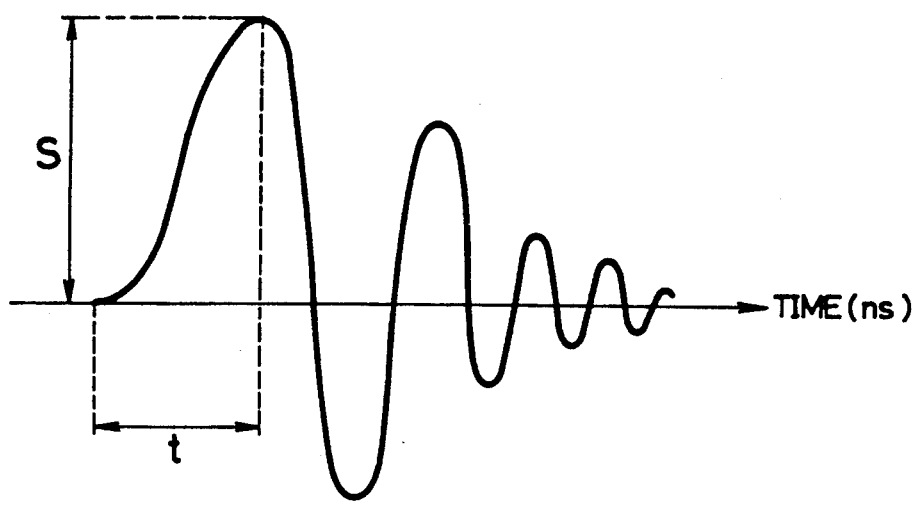

FIG. 3 shows a wave-form of the pseudo acoustic-emission waves thus observed.

In the acoustic-emission sensor of the present embodiment, rise time t is 1290 ns (rise time being the time taken to reach a peak from the time when signal reception of the pseudo acoustic-emission waves begins) and reception sensitivity S is 50 mV (reception sensitivity being a peak level in the rise time t of the pseudo acoustic-emission waves).

A second embodiment of the present invention is described hereinbelow, referring to FIG. 4. For the sake of convenience, members having the same function as in the aforementioned embodiment will be designated by the same reference numerals and their description will be omitted.

Figure 4:
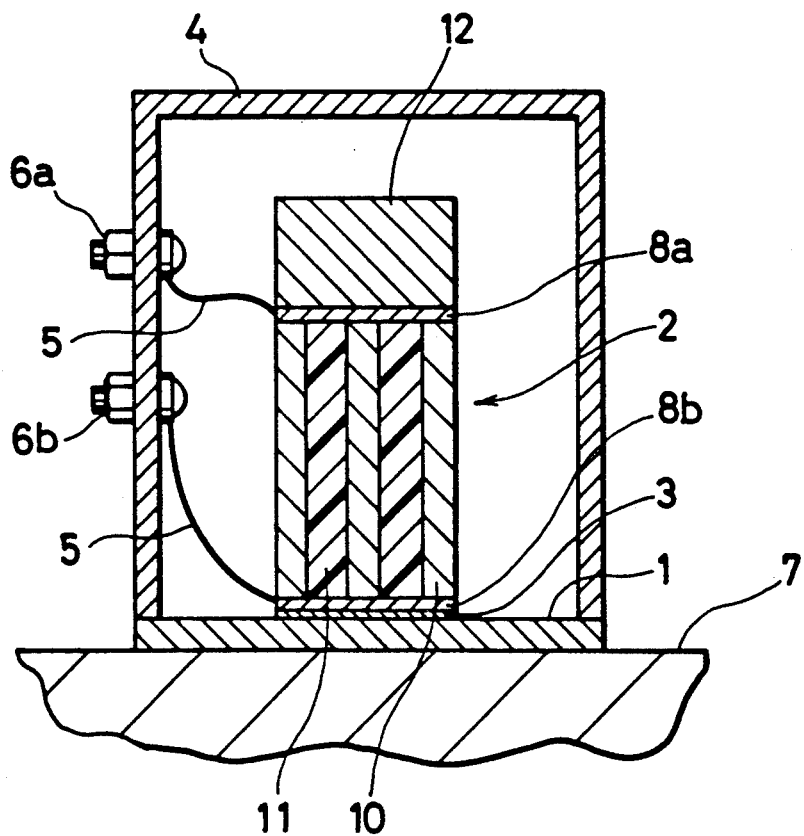
FIG. 4 shows a second embodiment of the present invention and is a longitudinal sectional view of an acoustic-emission sensor.

As shown in FIG. 4, an acoustic-emission sensor of the present embodiment comprises a weight 12 fixed on an electrode 8a, the electrode 8a being disposed on an upper end-face of a composite synthetic resin-ceramic piezoelectric element 2. In all other respects, the acoustic-emission sensor resembles the acoustic-emission sensor of the first embodiment.

With the above arrangement, the weight 12 is fixed on the electrode 8a, the electrode 8a being disposed on the end-face opposite to an end-face whereon a receiving plate 1 is provided. Consequently, when compression and tension of columnar ceramic piezoelectric bodies 10 take place in a longitudinal direction due to the acoustic-emission waves, movement of the composite synthetic resin-ceramic piezoelectric element 2 as a whole is suppressed due to the inertia of the weight 12. As a result, an amount of compression and tension of the columnar ceramic piezoelectric body 10 increases, causing a potential difference to develop between the columnar ceramic piezoelectric bodies 10. This increases a reception sensitivity S of the acoustic-emission sensor with respect to the acoustic-emission waves.

A third embodiment of the present invention is described hereinbelow, referring to FIGS. 5 and 6. For the sake of convenience, members having the same function as in the aforementioned embodiment will be designated by the same reference numerals and their description will be omitted.

Figure 5:
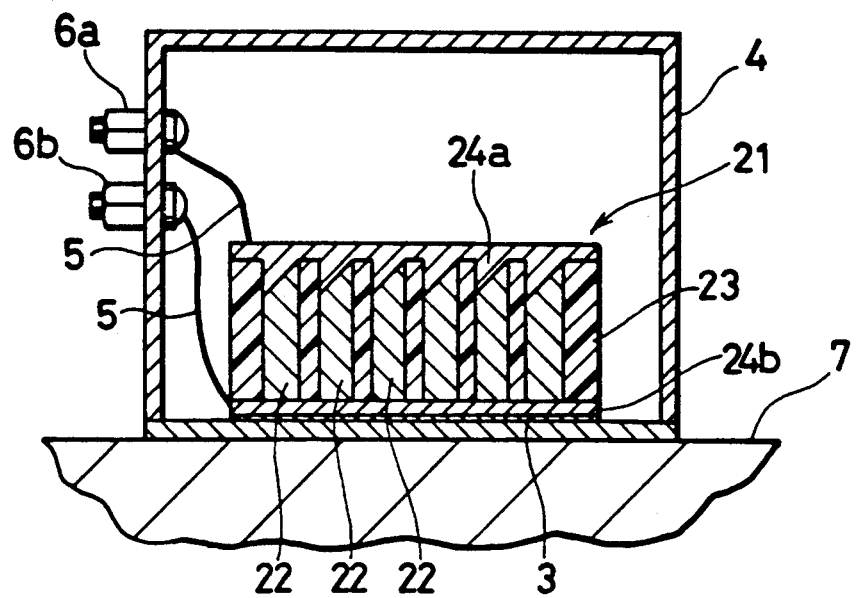
FIGS. 5 and 6 show a third embodiment of the present invention.
Figure 6:
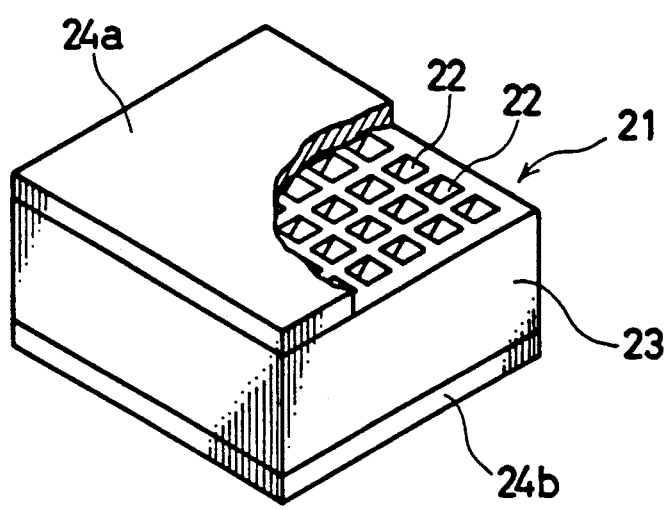

As shown in FIGS. 5 and 6, an acoustic-emission sensor of the present embodiment differs from the acoustic-emission sensor of the first embodiment (see FIG. 1) in that inclined faces are provided on upper sections of columnar ceramic piezoelectric bodies 22 which are disposed in a composite synthetic resin-ceramic piezoelectric element 21.

In other words, the composite synthetic resin-ceramic piezoelectric element 21 comprises the columnar ceramic piezoelectric bodies 22 which are quadrangular in a sectional view and have inclined faces provided on the upper sections thereof. The columnar ceramic piezoelectric bodies 22 are arranged in a longitudinal direction (an up-down direction in FIG. 5) in a synthetic-resin matrix 23 so as to be substantially parallel. Upper and lower end-faces of the columnar ceramic piezoelectric bodies 22 respectively have electrodes 24a and 24b disposed thereon. In each of the columnar ceramic piezoelectric bodies 22 there are piezoelectric crystal grains, a crystal axis of each of the piezoelectric crystal grains being oriented and polarized in the longitudinal direction.

In FIG. 6 the upper sections of the columnar ceramic piezoelectric bodies 22 are shown as having the inclined faces which are inclined at 45° with respect to the longitudinal direction. However, the upper section may equally be made into a truncated pyramid or truncated cone so that a curved inclined face or inclined faces is/are formed along the sides of a plateau-like peak. Alternatively, the upper section may be made into a hemispherical shape so that the entire upper surface becomes an inclined face having a curved surface; and so on, as necessary. The inclined face may equally be a level surface or a curved surface.

In all other respects, the acoustic-emission sensor of the present embodiment resembles the acoustic-emission sensor of the first embodiment.

With the above arrangement, since the inclined faces have been provided on the upper sections of the columnar ceramic piezoelectric bodies 22, apparent resonance points of the composite synthetic resin-ceramic piezoelectric element 21 increase. Accordingly, the acoustic-emission sensor of the present embodiment can receive acoustic-emission waves over a wide frequency range. Consequently, rise time t becomes shorter. In other words, the acoustic-emission sensor becomes more responsive.

A manufacturing method of a composite urethane rubber-PZT piezoelectric element as a specific example of the composite synthetic resin-ceramic piezoelectric element 21 is described hereinbelow. Performance of the acoustic-emission sensor using this composite urethane rubber-PZT piezoelectric element is also described.

As in the first embodiment, 32 PZT columns are first formed on a 5 mm-thick circular PZT plate section, each of the PZT columns being quadrangular in a sectional view and each measuring 1 mm×1 mm×5 mm. Then, in the present embodiment, the inclined faces are formed on the upper sections of the square-shaped columns at an angle of 45° with respect to a lower surface of the circular PZT plate section. Thereafter, as described in the first embodiment, a composite urethane rubber-PZT piezoelectric material is manufactured. This composite urethane rubber-PZT piezoelectric material comprises the 32 PZT columns which measure 1 mm×1 mm×4−3 mm and which have the inclined faces formed on the upper sections thereof. The rise time t of the acoustic-emission sensor comprising this composite urethane rubber-PZT piezoelectric body was measured in the same way as in the first embodiment and was found to be 1041 ns. As is evident, this rise time t is shorter than the rise time of 1290 ns achieved by the acoustic-emission sensor of the first embodiment comprising the columnar ceramic piezoelectric bodies 10 (see FIG. 1) which do not having inclined faces provided on upper sections thereof.

A fourth embodiment of the present invention is described hereinbelow, referring to FIGS. 7 to 10. For the sake of convenience, members having the same function as in the aforementioned embodiment will be designated by the same reference numerals and their description will be omitted.

Figure 7:
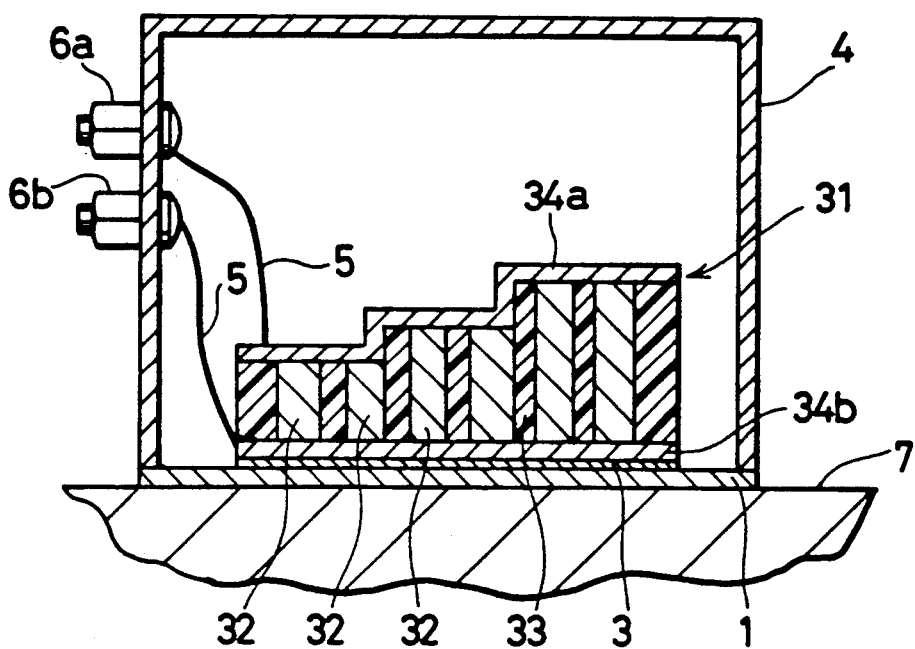
FIGS. 7 to 10 show a fourth embodiment of the present invention.
Figure 8:
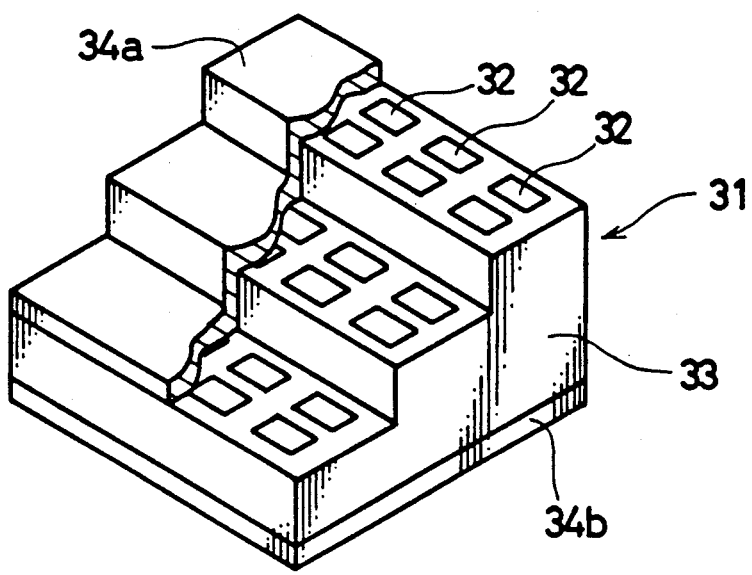

As shown in FIGS. 7 and 8, an acoustic-emission sensor of the present embodiment differs from the acoustic-emission sensor of the first embodiment (see FIG. 1) in that heights (lengths in a longitudinal direction) of columnar ceramic piezoelectric bodies 32 are not uniform, the columnar ceramic piezoelectric bodies 32 being disposed in a composite synthetic resin-ceramic piezoelectric element 31.

In other words, the composite synthetic resin-ceramic piezoelectric element 31 of the present embodiment comprises the columnar ceramic piezoelectric bodies 32 whose heights differ respectively in a left-hand section, a central section and a right-hand section of the composite synthetic resin-ceramic piezoelectric element 31. Consequently, an electrode 34b provided on a lower part thereof is level but an electrode 34a provided on an upper part thereof is three-stepped.

In all other respects, the acoustic-emission sensor of the present embodiment resembles the acoustic-emission sensor of the first embodiment.

Figure 9:
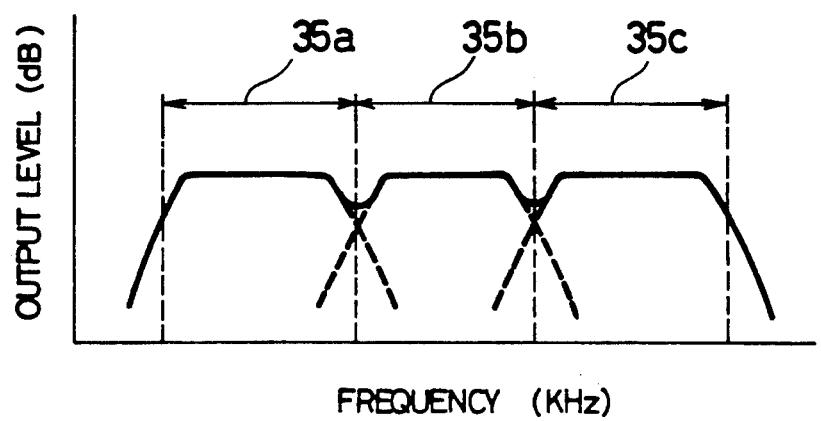

The acoustic-emission sensor of the present embodiment has three different resonant frequencies since the composite synthetic resin-ceramic piezoelectric element 31 in the acoustic-emission sensor comprises the columnar ceramic piezoelectric bodies 32 which have the three different heights, as described above. Consequently, the acoustic-emission sensor of the present embodiment approaches the ideal frequency characteristics of acoustic-emission sensors. That is, an output level of the acoustic-emission sensor of the present embodiment is substantially constant over a low-frequency band 35a, a medium-frequency band 35b, and a high-frequency band 35c, as shown in FIG. 9.

Figure 10:
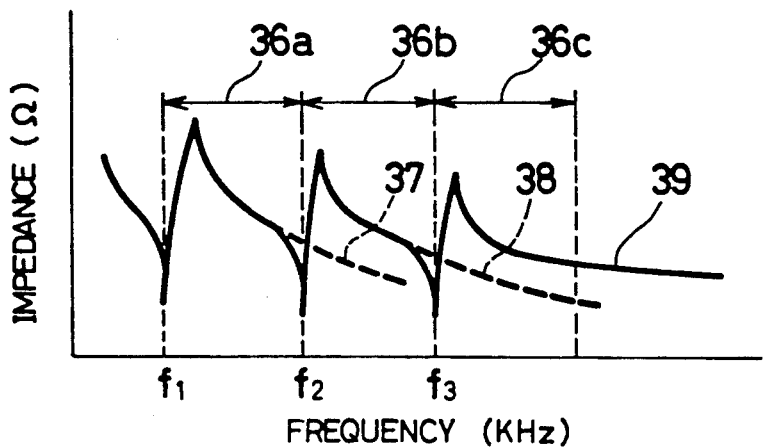

Regarding the fact that the acoustic-emission sensor of the present embodiment approaches the ideal frequency characteristics of acoustic-emission sensors, a description follows hereinbelow of frequency-dependence of an impedance of the acoustic-emission sensor, referring to FIG. 10.

Suppose that the heights of the columnar ceramic piezoelectric bodies 32 are all the same. The acoustic-emission sensor will then have a single resonance frequency $f_1$. In a frequency band lower than the resonance frequency $f_1$, the impedance of the acoustic-emission sensor decreases as the frequency increases. However, as shown in FIG. 10, at the resonance frequency $f_1$ the impedance first falls suddenly and steeply and then rises very high. Then, the impedance begins to fall along a curved line 37 as the frequency rises to a frequency band greater than the resonance frequency $f_1$. Since it is necessary to an extent to have a high impedance in order to detect the acoustic-emission waves and to achieve a specified output level, a detecting frequency band of this acoustic-emission sensor is limited to a low-frequency band 36a.

If the columnar ceramic piezoelectric bodies 32 have two different heights, the acoustic-emission sensor will have two resonance frequencies $f_1$ and $f_2$. If $f_1 < f_2$, then in a frequency band lower than the resonance frequency $f_2$ the impedance of the acoustic-emission sensor shows the same frequency-dependence as described above. At the resonance frequency $f_2$, the impedance again falls suddenly and steeply and then rises very high. Then, the impedance begins to fall along a curved line 38 as the frequency rises to a frequency band greater than the resonance frequency $f_2$. Here, in a frequency band which is higher than the resonance frequency $f_2$, the impedance is greater than in a case where the acoustic-emission sensor comprises the columnar ceramic piezoelectric bodies 32 which are of a uniform height. This is evident from a comparison of the curved line 37 with the curved line 38. Consequently, in the case where the columnar ceramic piezoelectric bodies 32 have the two different heights, the output level can be maintained at a higher frequency. In other words, the detecting frequency band increases and the acoustic-emission waves in the low-frequency band 36a and in a medium-frequency band 36b can be detected.

Further, if the columnar ceramic piezoelectric bodies 32 have three different heights, the acoustic-emission sensor will have three resonance frequencies $f_1$, $f_2$ and $f_3$. If $f_1 < f_2 < f_3$, then in a frequency band lower than the resonance frequency $f_3$ the impedance of the acoustic-emission sensor shows the same frequency-dependence as described above. At the resonance frequency $f_3$, the impedance falls suddenly and steeply and then rises very high. Then, the impedance begins to fall along a curved line 39 as the frequency rises to a frequency band greater than the resonance frequency $f_3$. Here, in a frequency band which is higher than the resonance frequency $f_3$, the impedance is greater than in a case where the acoustic-emission sensor comprises the columnar ceramic piezoelectric bodies 32 which have the two different heights. This is evident from a comparison of the curved line 38 with the curved line 39. Consequently, in the case where the columnar ceramic piezoelectric bodies 32 have the three different heights, the output level can be maintained at a yet higher frequency. In other words, the detecting frequency band increases still more so that the acoustic-emission waves in the low-frequency band 36a, in the medium-frequency band 36b and in a high-frequency band 36c can now be detected.

Thus, the frequency characteristics of the acoustic-emission sensor of the present embodiment approach the ideal frequency characteristics of an acoustic-emission sensor (see FIG. 9). The acoustic-emission sensor becomes more responsive when the detecting frequency band increases. As a result, pulse-shaped acoustic-emission waves which include many frequency components are faithfully received. Further, since rise time becomes shorter, a large acoustic-emission signal can be achieved. That is, acoustic-emission reception sensitivity S increases.

A manufacturing method of a composite urethane rubber-PZT piezoelectric element as a specific example of the composite synthetic resin-ceramic piezoelectric element 31 is described hereinbelow. Performance of the acoustic-emission sensor using this composite urethane rubber-PZT piezoelectric element is also described.

As in the first embodiment, 32 PZT columns are first formed on a 5 mm-thick circular PZT plate section, each of the PZT columns being quadrangular in a sectional view and each measuring 1 mm × 1 mm × 5 mm. Then, two rows of 10 PZT square columns at one extreme end of the circular PZT plate section are made 2 mm high, two rows of 12 PZT square columns in a central portion are made 3 mm high and remaining two rows of 10 PZT square columns are made 4 mm high. A fine-processed PZT material is thereby achieved. Thereafter, fine adjustment of the respective heights is carried out so that the respective frequencies are 860 KHz, 420 KHz and 350 KHz. The subsequent manufacturing process is the same as in the first embodiment.

When the rise time t and the reception sensitivity S of the acoustic-emission sensor thereby achieved were measured according to the same method as in the first embodiment, they were found to be 800 ns and 84 mV respectively.

By way of comparison, rise time t and reception sensitivity S were found to be 882 ns and 48 mV respectively in a case where an acoustic-emission sensor is manufactured by the same method as described above, this acoustic-emission sensor having 16 3 mm-high PZT columns located in a right-half and 16 4 mm-high PZT columns located in a left-half, among a total of 32 PZT columns which are square in a sectional view.

As is evident, the acoustic-emission sensor of the present embodiment (which comprises the columnar ceramic piezoelectric bodies 32 of different heights) is more responsive since it has a shorter rise time, substantially ⅝ that of the acoustic-emission sensor of the first embodiment in which the columnar ceramic piezoelectric bodies 10 are all of the same height.

Further, the acoustic-emission sensor, which comprises the columnar ceramic piezoelectric bodies 32 having three different heights, has 60% higher reception sensitivity S than both the acoustic-emission sensor comprising the columnar ceramic piezoelectric bodies 32 which have two different heights and the acoustic-emission sensor of the first embodiment in which the columnar ceramic piezoelectric bodies 10 are all of the same height.

The same effect may equally be achieved by having, for example, four different heights of the columnar ceramic piezoelectric bodies 32 instead of three. However, although the detecting frequency band will increase since resonance points increase, if the number of different heights is excessive then the number of columnar ceramic piezoelectric bodies 32 per every resonance point will decrease and the reception sensitivity S deteriorates.

A fifth embodiment of the present invention is described hereinbelow, referring to FIGS. 11 to 13. For the sake of convenience, members having the same function as in the aforementioned embodiment will be designated by the same reference numerals and their description will be omitted.

Figure 11:
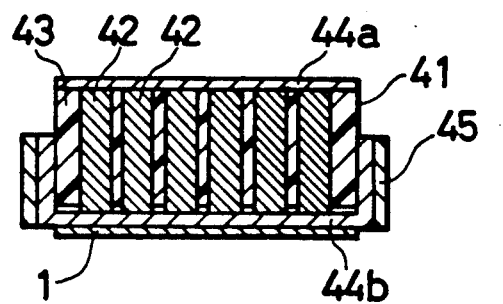
FIGS. 11 to 13 show a fifth embodiment of the present invention.
Figure 12:
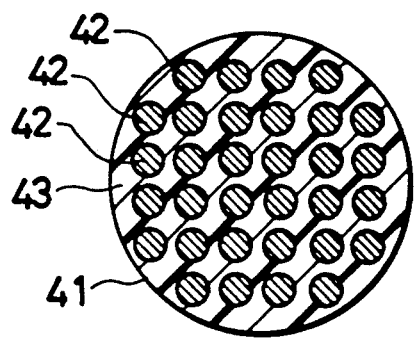
Figure 13:
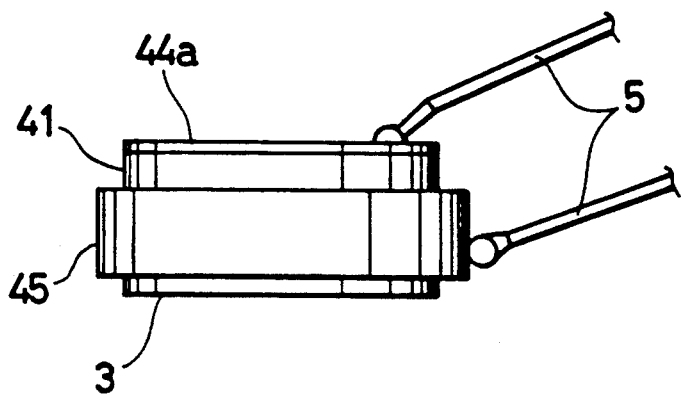

As shown in FIGS. 11 to 13, an acoustic-emission sensor of the present embodiment differs from the acoustic-emission sensor of the first embodiment (see FIG. 1) principally in that a composite synthetic resin-ceramic piezoelectric element 41 comprises circular-columnar ceramic piezoelectric bodies 42 and in that a lower-end electrode 44b covers half a side-face of a synthetic-resin matrix 43, a metal ring 45 being fitted thereon so as to be electrically connected to a side-face section of the electrode 44b.

In all other respects, the acoustic-emission sensor resembles the acoustic-emission sensor of the first embodiment.

With the above arrangement, since the circular-columnar ceramic piezoelectric bodies 42 do not possess anisotropy in a radial direction, oscillation of the circular-columnar ceramic piezoelectric bodies 42 in an axial direction is easily dispersed by the synthetic-resin matrix 43. Since the oscillation of the circular-columnar ceramic piezoelectric bodies 42 in the axial direction is easily dispersed, a transverse oscillation mode (oscillation mode in the radial direction) is not detected. Furthermore, lead wires 5 may be connected easily and reliably since the lead wires 5 are connected via the copper metal ring 45 and are not directly connected to the electrode 44b whereon a receiving plate 1 is fixed.

A manufacturing method of a composite urethane rubber-PZT piezoelectric element as a specific example of the composite synthetic resin-ceramic piezoelectric element 41 is described hereinbelow. Performance of the acoustic-emission sensor using this composite urethane rubber-PZT piezoelectric element is also described.

As in the first embodiment, 32 circular PZT columns (diameter 1 mm; length 4 mm) are regularly arranged to manufacture circular-columnar composite urethane rubber-PZT material. Silver paste is then applied on one end-face section and on a side-face section close to an other end-face. An electrode 44a as a silver electrode and a side-face section of an electrode 44b are then formed by carrying out baking processing for 30 minutes at 120° C. Using the sputtering method, a gold electrode is formed as the electrode 44b on the other end-face so as to be electrically connected to the silver electrode formed on the side-face section. A thin alumina diaphragm is adhered to a surface of the gold-electrode using an adhesive. The alumina diaphragm is 0.2 mm thick and serves as a receiving plate 1.

Then, the copper metal ring 45 (diameter 10 mm; height 3 mm) is fitted around the side-face section of the electrode 44b. Finally, lead wires 5 are soldered to the electrode 44a and the copper metal ring 45 to obtain the acoustic-emission sensor comprising the composite urethane rubber-PZT piezoelectric element.

When the rise time t and the reception sensitivity S of the acoustic-emission sensor thereby achieved are measured as was done in the first embodiment, these were found to be 1220 ns and 62 mV respectively.

Further, the piezoelectric constant $g_{33}$ and the mechanical quality coefficient $Q_M$ were found by measuring resonance characteristics using an impedance meter (Yokogawa-Hewlett-Packard Company; Model No. 4194A). The piezoelectric constant $g_{33}$ was found to be $117 \times 10^{-3}$ Vm/N and the mechanical quality coefficient $Q_M$ was found to be 3.

By way of comparison, consider a case where an acoustic-emission sensor is manufactured by the same method as described above and the circular-columnar ceramic piezoelectric bodies 42 are replaced by columnar ceramic piezoelectric bodies which are quadrangular in a sectional view. In this case, when the rise time t, the reception sensitivity S, the piezoelectric constant $g_{33}$ and the mechanical quality coefficient $Q_M$ were measured by the same method as described above, these were found to be 1290 ns, 68 mV, $118 \times 10^{-3}$ Vm/N and 9 respectively.

It is evident from the above results that the mechanical quality coefficient $Q_M$ in the case of the acoustic-emission sensor of the present embodiment is ⅓ of the mechanical quality coefficient $Q_M$ obtained in the case where the acoustic-emission sensor comprises the columnar ceramic piezoelectric bodies which are quadrangular in a sectional view. This shows that reverberant sound in the composite synthetic resin-ceramic piezoelectric element 41 is rapidly attenuated and that separation characteristics of detection signals have clearly improved. In other words, even if a large number of acoustic emission waves are received in a short period of time, the detection signals do not overlap so easily. Furthermore, in this case the rise time t, the reception sensitivity S and the piezoelectric constant $g_{33}$ have substantially the same characteristics as in the case of the acoustic-emission sensor comprising the columnar ceramic piezoelectric bodies which are quadrangular in a sectional view.

A sixth embodiment of the present invention is described hereinbelow, referring to FIGS. 14 and 15. For the sake of convenience, members having the same function as in the aforementioned embodiment will be designated by the same reference numerals and their description will be omitted.

Figure 14:
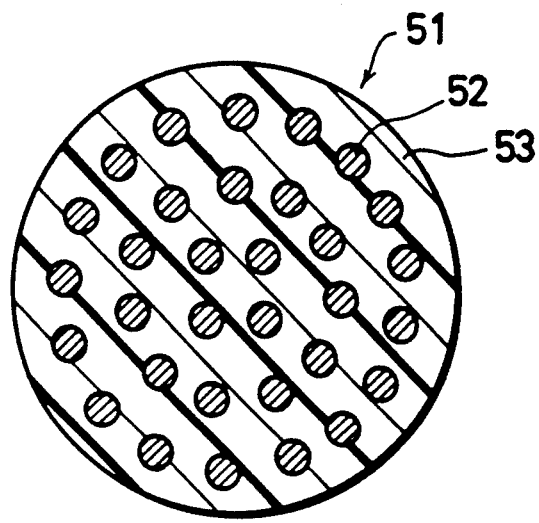
FIGS. 14 and 15 show a sixth embodiment of the present invention.

As shown in FIG. 14, an acoustic-emission sensor of the present embodiment differs from the acoustic-emission sensor of the fifth embodiment (see FIG. 12) in that a composite synthetic resin-ceramic piezoelectric element 51 is used, the composite synthetic resin-ceramic piezoelectric element 51 comprising circular-columnar ceramic piezoelectric bodies 52 arranged concentrically in a synthetic-resin matrix 53.

In all other respects, the acoustic-emission sensor resembles the acoustic-emission sensor of the fifth embodiment.

With the above arrangement, since the circular-columnar ceramic piezoelectric bodies 52 are arranged concentrically in the synthetic-resin matrix 53, anisotropy almost completely disappears among the circular-columnar ceramic piezoelectric bodies 52. Consequently, attenuation of the longitudinal oscillation mode due to transverse oscillations induced by longitudinal oscillations does not occur so easily, thereby raising reception sensitivity S.

A manufacturing method of a composite urethane rubber-PZT piezoelectric element as a specific example of the composite synthetic resin-ceramic piezoelectric element 51 is described hereinbelow. Performance of an acoustic-emission sensor using this composite urethane rubber-PZT piezoelectric element is also described.

As in the fifth embodiment, 32 circular PZT columns (diameter 0.7 mm; length 4 mm) are regularly arranged concentrically to manufacture the circular-columnar composite urethane rubber-PZT piezoelectric element. Counting in sequence from an inner side, each concentric circle is made respectively by 4, 11 and 17 circular columns.

When a rise time t, reception sensitivity S, and piezoelectric constant $g_{33}$ of the acoustic-emission sensor comprising the composite urethane rubber-PZT piezoelectric element were measured by the same method as in the fifth embodiment, these were found to be 1080 ns, 161 mV and $87 \times 10^{-3}$ Vm/N respectively.

In the case where the acoustic-emission sensor comprises the circular-columnar composite urethane rubber-PZT piezoelectric element in which the circular-columnar ceramic piezoelectric bodies 52, made from sintered PZT material, are arranged concentrically, although the piezoelectric constant $g_{33}$ is lower than that of the acoustic-emission sensor of the fifth embodiment which comprises the circular-columnar ceramic piezoelectric bodies 42 arranged in a checkerboard pattern, the reception sensitivity S rises to over twice as much and the rise time t also becomes slightly shorter.

The rise in the reception sensitivity S is due to the concentric arrangement of the circular-columnar ceramic piezoelectric bodies 52. The reception sensitivity S rises because anisotropy among the circular-columnar ceramic piezoelectric bodies 52 practically disappears.

Figure 15:
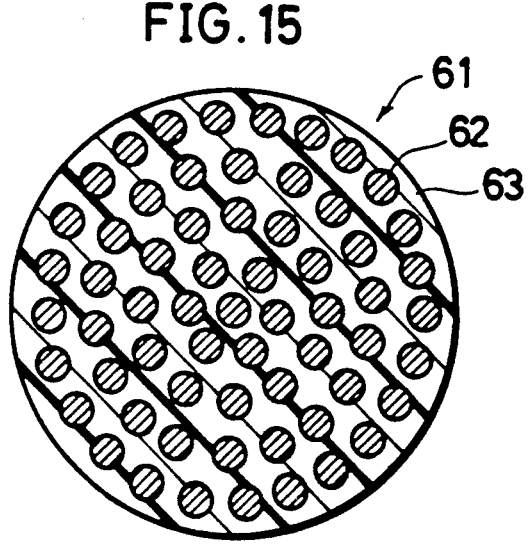

As shown in FIG. 15, an acoustic-emission sensor comprising a composite urethane rubber-PZT piezoelectric element is manufactured as described above, the composite urethane rubber-PZT piezoelectric element having 62 circular-columnar (diameter 0.7 mm; length 4 mm) ceramic piezoelectric bodies 62 made of PZT and arranged concentrically in a synthetic-resin matrix 63 made of urethane rubber. Counting in sequence from an inner side, each concentric circle is made respectively by 6, 12, 18 and 25 circular columns, with one of the circular columns making up a center thereof. When a rise time t, reception sensitivity S, and piezoelectric constant $g_{33}$ of this acoustic-emission sensor were measured by the same method as described earlier, these were found to be 1066 ns, 156 mV and $107 \times 10^{-3}$ Vm/N respectively.

Accordingly, the reception sensitivity S is substantially the same for both the acoustic-emission sensor comprising the composite synthetic resin-ceramic piezoelectric element 51 which has the 32 circular-columnar ceramic piezoelectric bodies 52, and the acoustic-emission sensor comprising the composite synthetic resin-ceramic piezoelectric element 61 which has the 62 circular-columnar ceramic piezoelectric bodies 62. In other words, the increase in reception sensitivity S depends on whether the arrangement of the ceramic piezoelectric bodies is concentric or not, not just on the number of ceramic piezoelectric bodies (in this case, the circular-columnar ceramic piezoelectric bodies 52 and 62) which are used to make a composite synthetic resin-ceramic piezoelectric element.

A seventh embodiment of the present invention is described hereinbelow, referring to FIGS. 16 and 17. For the sake of convenience, members having the same function as in the aforementioned embodiment will be designated by the same reference numerals and their description will be omitted.

Figure 16:
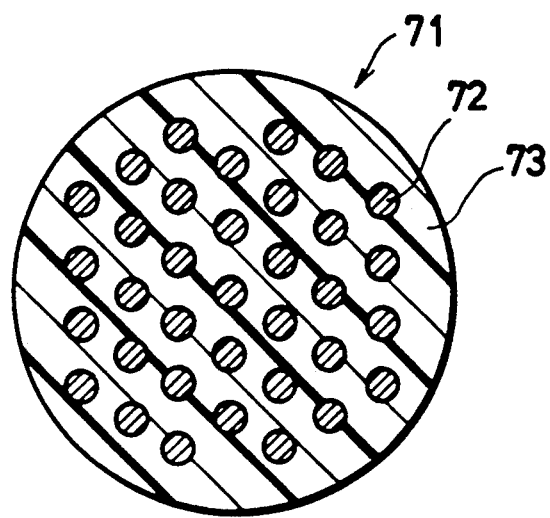
FIGS. 16 and 17 show a seventh embodiment of the present invention.

As shown in FIG. 16, an acoustic-emission sensor of the present embodiment differs from the acoustic-emission sensor of the fifth embodiment (see FIG. 12) in that a composite synthetic resin-ceramic piezoelectric element 71 is used, the composite synthetic resin-ceramic piezoelectric element 71 comprising circular-columnar ceramic piezoelectric bodies 72 arranged in a synthetic-resin matrix 73 so as to be in a closest-packed configuration.

In all other respects, the acoustic-emission sensor resembles the acoustic-emission sensor of the fifth embodiment.

With the above arrangement, anisotropy in a radial direction is diminished compared to the acoustic-emission sensor of the fifth embodiment for the following reason. Since the circular-columnar ceramic piezoelectric bodies 72 are arranged in the synthetic-resin matrix 73 so as to be in the closest-packed configuration, six circular-columnar ceramic piezoelectric bodies 72 surround each of the circular-columnar ceramic piezoelectric bodies 72, excluding the circular-columnar ceramic piezoelectric bodies 72 which lie on an outermost side. These surrounding circular-columnar ceramic piezoelectric bodies 72 form an orthohexagonal shape. Consequently, the same properties appear in the radial direction every 60° about an axis (longitudinal direction) of any of the circular-columnar ceramic piezoelectric bodies 72. On the other hand, in the fifth embodiment where the circular-columnar ceramic piezoelectric bodies 42 are arranged in the checkerboard pattern, the same properties do not appear in a radial direction except every 90° about an axis (longitudinal direction) of each of the circular-columnar ceramic piezoelectric bodies 42, excluding the circular-columnar ceramic piezoelectric bodies 42 which lie on an outermost side. As a result, in the case where the closest-packed configuration is adopted, anisotropy in the radial direction is diminished in comparison to the case where the checkerboard pattern is adopted.

In the same way as in the previous embodiment, a manufacturing method of a composite urethane rubber-PZT piezoelectric element as a specific example of the composite synthetic resin-ceramic piezoelectric element 71 is described hereinbelow. Performance of an acoustic-emission sensor using this composite urethane rubber-PZT piezoelectric element is also described.

As in the previous embodiment, 35 circular PZT columns (diameter 0.9 mm; length 4 mm) are regularly arranged in the closest-packed configuration in the synthetic-resin matrix 73 made from urethane rubber to manufacture the composite urethane rubber-PZT piezoelectric element. When a rise time t, reception sensitivity S, piezoelectric constant $g_{33}$ and mechanical quality coefficient $Q_M$ of the acoustic-emission sensor comprising the composite urethane rubber-PZT piezoelectric element were measured by the same method as described earlier, these were found to be 1250 ns, 80 mV, $121 \times 10^{-3}$ Vm/N and 2 respectively.

Comparing the acoustic-emission sensor comprising the composite synthetic resin-ceramic piezoelectric element in which the circular-columnar ceramic piezoelectric bodies 72 are arranged in the closest-packed configuration, with the acoustic-emission sensor of the fifth embodiment in which the circular-columnar ceramic piezoelectric bodies 42 are arranged in the checkerboard pattern, it will be noticed that although the rise time t, the piezoelectric constant $g_{33}$ and the mechanical quality coefficient $Q_M$ remain substantially unchanged, the reception sensitivity S clearly increases. The reception sensitivity S increases because attenuation of a longitudinal oscillation mode due to transverse oscillations induced by longitudinal oscillations does not occur so easily. This is due to the fact that the anisotropy among the circular-columnar ceramic piezoelectric bodies 72 which are arranged in the closest-packed configuration decreases compared to the case where the arrangement is in the checkerboard pattern.

Figure 17:
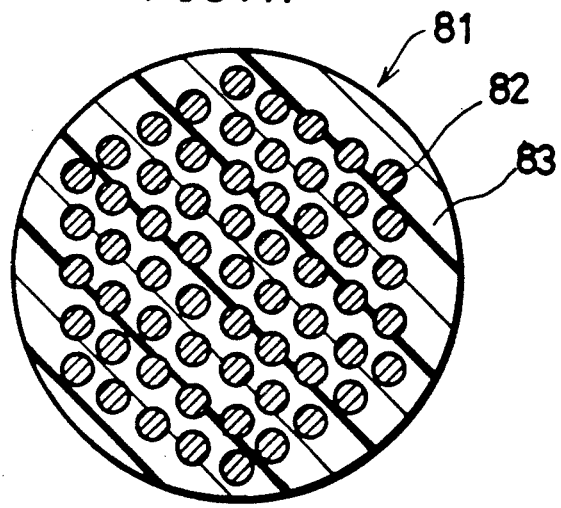

Further, as shown in FIG. 17, 61 circular PZT columns (diameter 0.7 mm; length 4 mm) may be regularly arranged in a closest-packed configuration in a synthetic-resin matrix 83 made from urethane rubber to manufacture a composite urethane rubber-PZT piezoelectric element in the same manner as described earlier. When a rise time t, reception sensitivity S, piezoelectric constant $g_{33}$ and mechanical quality coefficient $Q_M$ of an acoustic-emission sensor comprising this composite urethane rubber-PZT piezoelectric element were measured by the same method as described earlier, these were found to be 1200 ns, 130 mV, $119 \times 10^{-3}$ Vm/N and 3 respectively.

Comparing this acoustic-emission sensor which comprises a composite synthetic resin-ceramic piezoelectric element 81 made from 61 ceramic piezoelectric bodies 82, with the acoustic-emission sensor comprising the composite synthetic resin-ceramic piezoelectric element 71 made from the 35 circular-columnar ceramic piezoelectric bodies 72, it will be seen that the reception sensitivity S is greater by over 50% in the case of the acoustic-emission sensor comprising the composite synthetic resin-ceramic piezoelectric element 81. The increase in the reception sensitivity S is not because of an increase in the number of ceramic piezoelectric bodies but, as described in the previous embodiment, because of the ceramic piezoelectric bodies being arranged in the closest-packed configuration.

In other words, in the case of the composite synthetic resin-ceramic piezoelectric element 81 which comprises the ceramic piezoelectric bodies 82, the ceramic piezoelectric bodies 82 located in an outermost-side represent a smaller overall percentage than an overall percentage represented by the circular-columnar ceramic piezoelectric bodies 72 located in the outermost-side of the composite synthetic resin-ceramic piezoelectric element 71. This causes anisotropy among the ceramic piezoelectric bodies 82 to decrease further, resulting in the higher reception sensitivity S.

An eighth embodiment of the present invention is described hereinbelow, referring to FIGS. 18 to 22. For the sake of convenience, members having the same function as in the aforementioned embodiment will be designated by the same reference numerals and their description will be omitted.

Figure 18:
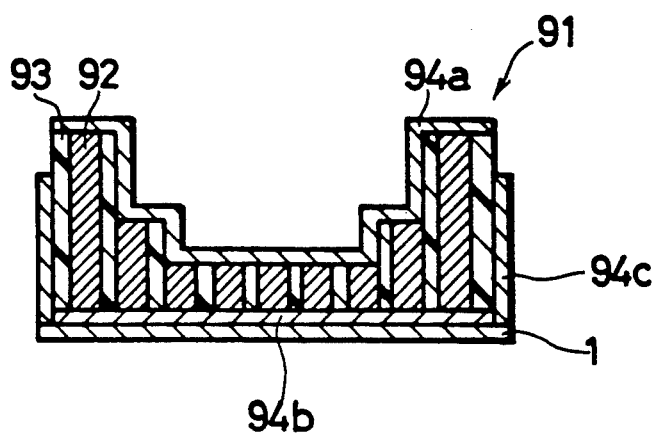
FIGS. 18 to 22 show an eighth embodiment of the present invention.
Figure 19:
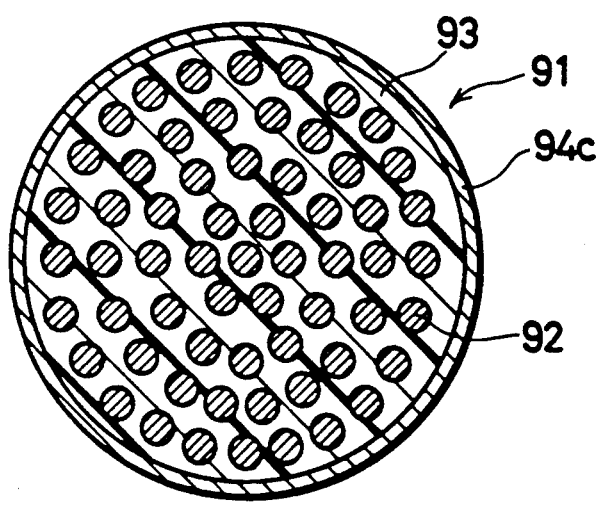

As shown in FIGS. 18 and 19, an acoustic-emission sensor of the present embodiment differs from the acoustic-emission sensor of the sixth embodiment (see FIG. 14) in that a composite synthetic resin-ceramic piezoelectric element 91 is used, the composite synthetic resin-ceramic piezoelectric element 91 comprising circular-columnar ceramic piezoelectric bodies 92 of three different heights wherein the circular-columnar ceramic piezoelectric bodies 92 of the same height are concentrically arranged in a synthetic-resin matrix 93.

That is, in the composite synthetic resin-ceramic piezoelectric element 91 of the present embodiment, each of the circular-columnar ceramic piezoelectric bodies 92 which form any one of the concentric circles have the same height. Further, the circular-columnar ceramic piezoelectric bodies 92 are arranged so that the closer a concentric circle is to an outer side, the greater is the height of the circular-columnar ceramic piezoelectric bodies 92 which form that concentric circle. Consequently, an electrode 94b provided on a lower part is level but an electrode 94a provided on an upper part is three-stepped. An electrode 94c provided on a side face is connected to the electrode 94b.

In all other respects, the acoustic-emission sensor resembles the acoustic-emission sensor of the sixth embodiment.

Arranging the circular-columnar ceramic piezoelectric bodies 92 concentrically means arranging them on circumferences of concentric circles whose center is a center of the composite synthetic resin-ceramic piezoelectric element 91. Naturally, it is impossible to form a perfect circle by arranging a limited number of the circular-columnar ceramic piezoelectric bodies 92 in this manner. Therefore, when the circular-columnar ceramic piezoelectric bodies 92 of the same height are disposed on the circumferences of each of the concentric circles, i.e., equidistantly from the center of the composite synthetic resin-ceramic piezoelectric element 91, strictly speaking the circular-columnar ceramic piezoelectric bodies 92 form polygons, not circles.

With the above arrangement, the acoustic-emission sensor of the present embodiment acts as a so-called resonance-dispersion type sensor since the composite synthetic resin-ceramic piezoelectric element 91 used therein comprises the circular-columnar ceramic piezoelectric bodies 92 which have different heights: the acoustic-emission sensor has a plurality of different resonance frequencies (resonance points) which correspond to the different heights of the circular-columnar ceramic piezoelectric bodies 92. Consequently, a detecting frequency band of the acoustic-emission sensor increases and, since resonance is being employed, a satisfactory reception sensitivity S is achieved. Further, the reception sensitivity S does not depend much on a reception direction since the circular-columnar ceramic piezoelectric bodies 92 are disposed concentrically in the synthetic-resin matrix 94.

A manufacturing method of a composite urethane rubber-PZT piezoelectric element as a specific example of the composite synthetic resin-ceramic piezoelectric element 91 is described hereinbelow. Performance of an acoustic-emission sensor 91a using this composite urethane rubber-PZT piezoelectric element is also described.

Circular-columnar (diameter 10 mm; length 6 mm) polarized and sintered PZT (produced by Honda Electronics Company; model number HC-50GS; relative dielectric constant = 1050; piezoelectric constant $g_{33} = 32 \times 10^{-3}$ Vm/N; electromechanical coupling factor $k_{33} = 67\%$; mechanical quality coefficient $Q_M = 1000$) is used as material for the circular-columnar ceramic piezoelectric bodies 92. A fine-processed PZT material is achieved by the following process. A total of 61 circular columns of diameter 0.7 mm and respective lengths 4 mm, 2 mm and 1 mm are formed to be arranged concentrically on a 2 mm-thick circular PZT plate section. Diameters of the concentric circles in sequence from an outermost side are respectively 8.5 mm, 6.4 mm, 4.3 mm and 2.1 mm. The concentric circles are made from circular-columnar PZT which are, respectively, 24 in number and 4 mm high, 18 in number and 2 mm high, 12 in number and 1 mm high and 6 in number and 1 mm high. One 1 mm-high circular-columnar PZT is formed in the center. Thereafter, the acoustic-emission sensor 91a comprising the composite synthetic resin-ceramic piezoelectric element is achieved by the same manufacturing method as described in the fifth embodiment.

The frequency characteristics of the acoustic-emission sensor 91a were determined by generating pseudo acoustic-emission waves by pressing down and breaking a pencil core 95 (produced by Pentel; hardness 2H; diameter 0.5 mm). The pseudo acoustic-emission waves are received by the acoustic-emission sensor 91a and an output voltage is measured.

Figure 20:
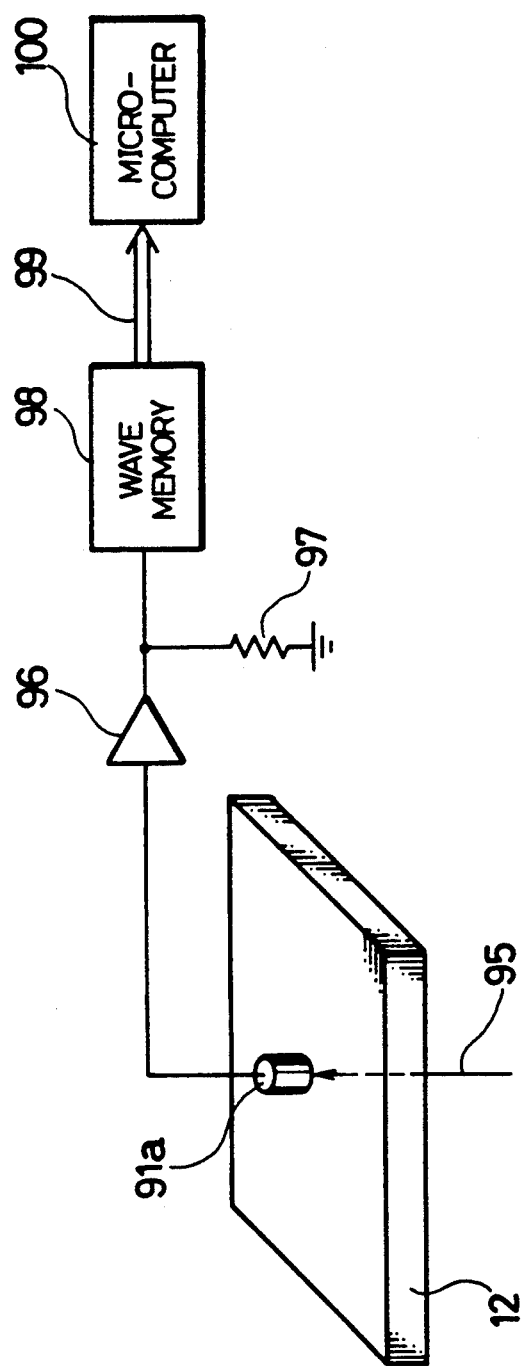

FIG. 20 shows a schematic configuration of a measuring instrument.

The measuring instrument comprises a transmission medium 12 (made of high-tensile aluminum alloy, JIS: Thick plate no. 7475; dimensions: 400 mm × 400 mm × 60 mm) for transmitting the pseudo acoustic-emission waves; the acoustic-emission sensor 91a which is firmly placed on an approximate center of the transmission medium 12; a preamplifier 96 (produced by NF Circuit Design Block Company; model NF9913S; amplification factor 20 dB) for amplifying an output of the acoustic-emission sensor 91a; a wave memory 98 (produced by Japan Physical Acoustics Company; model DL2120) for storing an output wave-form of the preamplifier 96; a terminating resistance 97 for impedance matching provided at an input side of the wave memory 98; and a microcomputer 100 (produced by Hewlett-Packard Company; model HP216) for receiving data stored by the wave memory 98 via an interface line 99 (GP-IB (General Purpose Interface Bus) and finding a frequency spectrum by carrying out a Fourier transformation.

With the above arrangement, the pencil core 95 is pressed down by a lower surface of the transmission medium 12 and broken. The pseudo acoustic-emission waves thereby generated are received by the acoustic-emission sensor 91a disposed on an upper surface of the transmission medium 12. A detected signal is amplified at the preamplifier 96 and then entered into the wave memory 98 at a fixed timing. The detected signal thereby entered into the wave memory 98 is sent to the microcomputer 100 via the interface line 99. Fourier transformation is then carried out in the microcomputer 100. Accordingly, a frequency spectrum showing frequency-dependence of the output voltage of the acoustic-emission sensor 91a is achieved.

In order to compare frequency characteristics, as a first example for comparison the same measurements were carried out using the single-resonance type acoustic-emission sensor described earlier which comprises the 61 uniformly 4 mm-high circular PZT columns (diameter 0.7 mm). The single-resonance type acoustic-emission sensor was manufactured using the same method and materials as described above.

The same measurements were carried out similarly with a second example and a third example for comparing frequency characteristics. Here, instruments used were a miniature single-resonance type acoustic-emission sensor (Physical Acoustics Company; product name PICO; diameter 3.5 mm; length 4.7 mm) as the second example and a wide-band non-resonance type acoustic-emission sensor (produced by Fuji Ceramics Company; calibration reference instrument REF10M; frequency band 0-10 MHz) as the third example, both available on the market.

Figure 21:
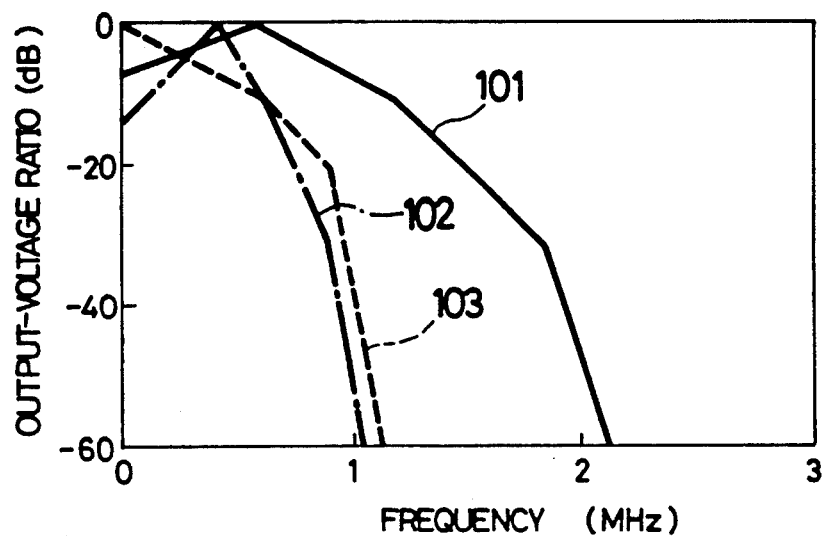
Figure 22:
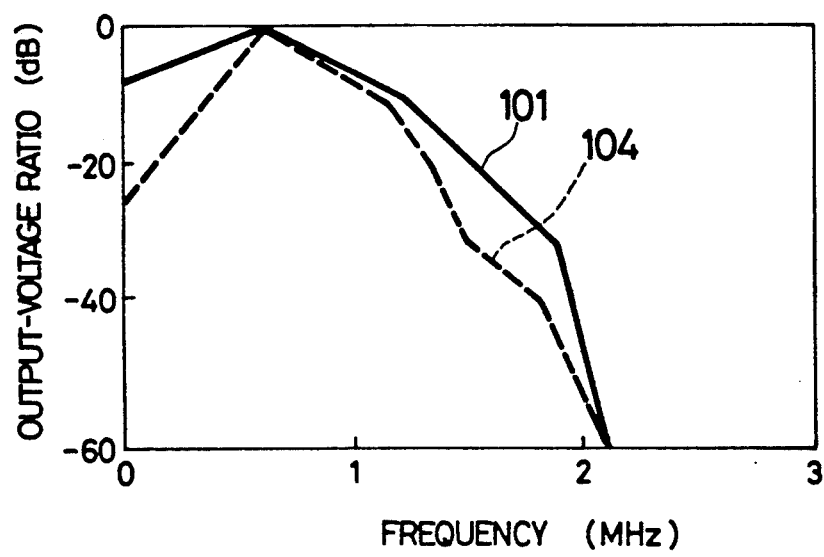

Results of the measurements are shown in FIGS. 21 and 22. A longitudinal axis is the output-voltage ratio of the detected signal and a transverse axis is the frequency.

FIG. 21 compares the frequency spectrum produced by the resonance-dispersion type acoustic-emission sensor 91a with the frequency spectra produced by the single-resonance type acoustic-emission sensors. A curved line 101 corresponds to the resonance-dispersion type acoustic-emission sensor 91a of the present embodiment and curved lines 102 and 103 respectively correspond to the single-resonance type acoustic-emission sensors (the first and second examples).

As is evident from the diagram, when the output-voltage ratio is attenuated to −60 dB, the frequency in the case of both the acoustic-emission sensor of the first example and the acoustic-emission sensor of the second example is approximately 1 MHz. However, the frequency in the case of the acoustic-emission sensor 91a of the present embodiment at −60 dB is approximately 2 MHz. Thus, the detecting frequency band is approximately doubled in the case of the acoustic-emission sensor 91a. This increase in the frequency band is a result of the resonance dispersion. In other words, the detecting frequency band increases in the resonance-dispersion type acoustic-emission sensor 91a due to the plurality of different resonance frequencies present therein.

FIG. 22 compares the frequency spectrum produced by the resonance-dispersion type acoustic-emission sensor 91a with the frequency spectrum produced by the wide-band non-resonance type acoustic-emission sensor (the third example). A curved line 101 corresponds, as in FIG. 21, to the resonance-dispersion type acoustic-emission sensor 91a of the present embodiment and a curved line 104 corresponds to the wide-band non-resonance type acoustic-emission sensor (the third example).

When the output-voltage ratio is attenuated to −60 dB, the frequency in the case of both the acoustic-emission sensor 91a of the present embodiment and the wide-band non-resonance type acoustic-emission sensor of the third example is approximately 2 MHz. However, in a high-frequency band of 1-2 MHz and in a low-frequency band lying below 500 kHz, a fall in the output-voltage ratio is greater in the case of the wide-band non-resonance type acoustic-emission sensor.

The output-voltage ratio falls in the high-frequency band and the low-frequency band in the case of the wide-band non-resonance type acoustic-emission sensor because a wide frequency band is achieved by suppressing resonance points using damping material made from resin, the damping material being made to press down on piezoelectric bodies. As against this, in the resonance-dispersion type acoustic-emission sensor 91a of the present embodiment, the circular-columnar ceramic piezoelectric bodies 92 (FIG. 18) having different heights are provided. This gives rise to resonance points in each of the low, medium and high frequency ranges respectively. Consequently, the fall in the output-voltage ratio in any of the frequency ranges is comparatively low. A wide-band and even detecting frequency spectrum is thereby achieved. Furthermore, since the measurement results were evaluated using the same measurement system (see FIG. 20), the output-voltage ratio can be compared. That is, the acoustic-emission sensor 91a of the present embodiment has a higher sensitivity in the frequency band of 0-2 MHz than the wide-band non-resonance type acoustic-emission sensor of the third example.

A ninth embodiment of the present invention is described hereinbelow, referring to FIGS. 23 to 25. For the sake of convenience, members having the same function as in the aforementioned embodiment will be designated by the same reference numerals and their description will be omitted.

Figure 23:
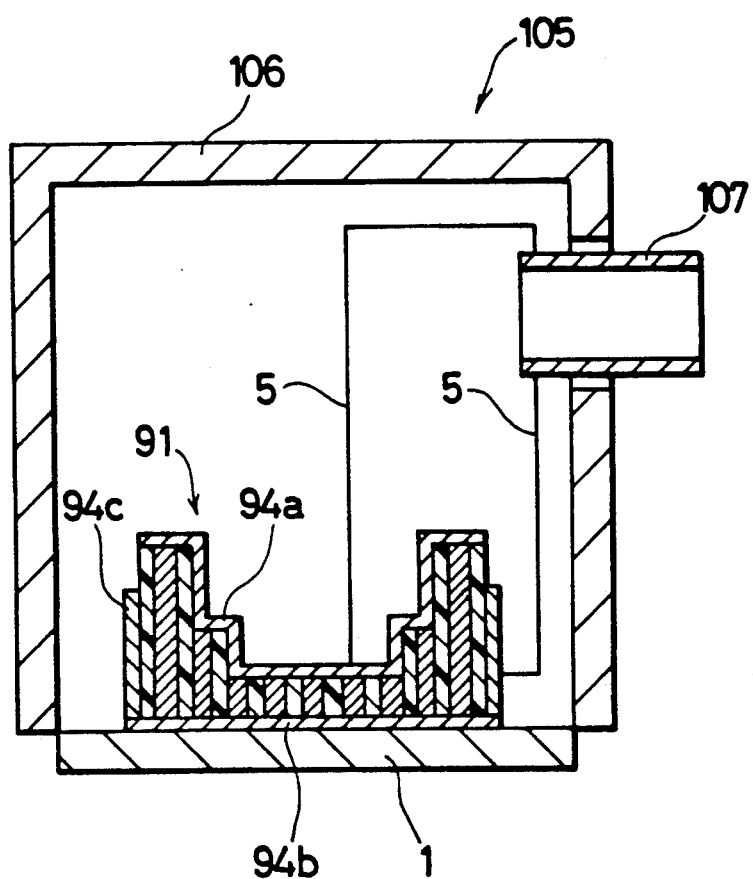
FIGS. 23 to 25 show a ninth embodiment of the present invention.

As shown in FIG. 23, an acoustic-emission sensor 105 of the present embodiment differs from the acoustic-emission sensor of the eighth embodiment (see FIG. 18) in that a composite synthetic resin-ceramic piezoelectric element 91 is housed in a metal housing (case) 106.

The acoustic-emission sensor 105 comprises a receiving plate 1, the composite synthetic resin-ceramic piezoelectric element 91 which is provided on the receiving plate 1, the metal housing 106 for shielding against external noise and for protecting the composite synthetic resin-ceramic piezoelectric element 91, and a connector 107 for releasing signals. The receiving plate 1 is fixed to the metal housing 106, by adhesive for example.

Electrodes 94a and 94c of the composite synthetic resin-ceramic piezoelectric element 91 are connected to the connector 107 by lead wires 5.

In all other respects, the acoustic-emission sensor resembles the acoustic-emission sensor of the eighth embodiment.

With the above arrangement, the metal housing 106 not only serves to shield against external noise and protect the composite synthetic resin-ceramic piezoelectric element 91 but also to fix the composite synthetic resin-ceramic piezoelectric element 91 to a test material via the receiving plate 1. That is, the relatively heavy weight of the metal housing 106 which acts downwards on the receiving plate 1 serves two functions. First, it prevents the acoustic-emission sensor 105 from slipping off the test material and second, it improves the sensitivity of the acoustic-emission sensor 105 in a high frequency band since unwanted reverberations generated in the composite synthetic resin-ceramic piezoelectric element 91 are attenuated due to reduced proper oscillation of the receiving plate 1.

Specifically, the metal housing 106 may be made of material such as aluminum or stainless steel.

On testing the acoustic-emission sensor 105 comprising the metal housing 106 which covers the composite synthetic resin-ceramic piezoelectric element 91 (described in the eighth embodiment), it was found that frequency characteristics thereof could be measured more precisely.

Figure 24:
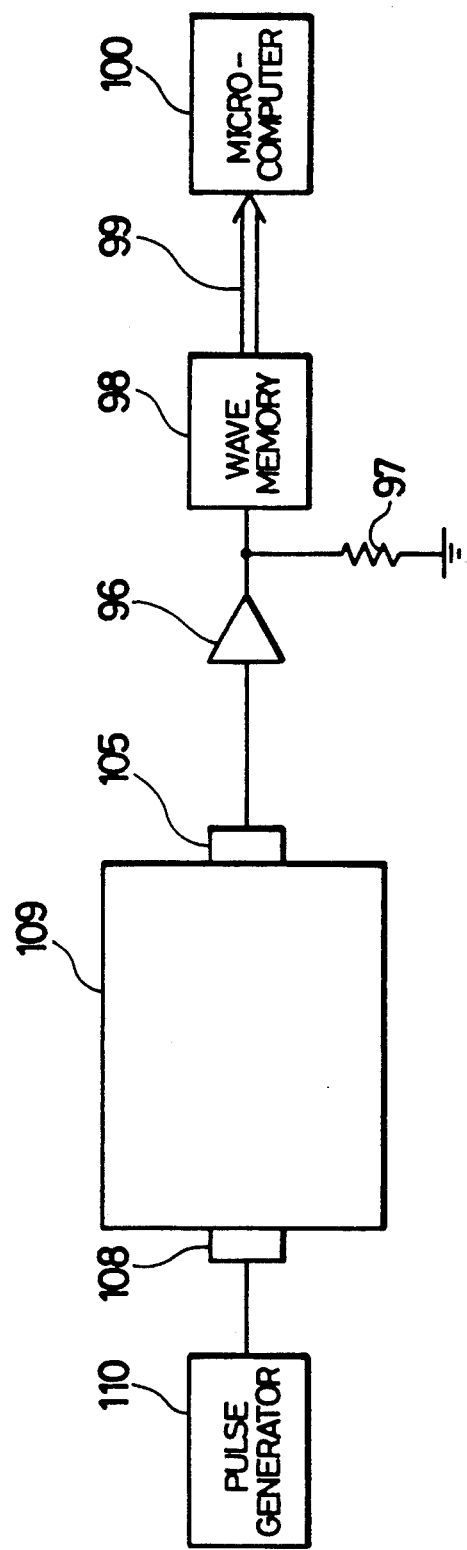

As shown by a block diagram in FIG. 24, a measuring instrument comprises a pulse generator 110 for generating electric pulses of several different frequencies, a sound-source sensor 108 for converting the electric pulses released by the pulse generator 110 into longitudinal ultrasonic wave pulses, a transmission medium 109 for the ultrasonic wave pulses, the acoustic-emission sensor 105 for receiving the ultrasonic wave pulses, a preamplifier 96 for amplifying an output of the acoustic-emission sensor 105, a wave memory 98 for storing an output wave-form of the preamplifier 96, a terminating resistance 97 for impedance matching provided at an input side of the wave memory 98, and a microcomputer 100 for receiving data stored by the wave memory 98 via an interface line 99 and finding a frequency spectrum. The sound-source sensor 108 and the acoustic-emission sensor 105 are disposed on opposite sides of the transmission medium 109 to be directly opposite to each other. An iron block is used here as the transmission medium 109 but an aluminum block may equally be used.

With the above arrangement, instead of generating pseudo acoustic-emission waves by pressing down and breaking a pencil core, pulses are generated by the pulse generator 110 and the sound-source sensor 108. The pulses have a constant amplitude irrespective of a frequency thereof. That is, the pulse generator 110 first generates the electric pulses having frequencies lying in a band of 100 KHz–2000 KHz; the electric pulses are then converted into the ultrasonic wave pulses in the sound-source sensor 108; and then, the ultrasonic wave pulses are received by the acoustic-emission sensor 105. Thus, a frequency spectrum showing frequency-dependence of the sensitivity of the acoustic-emission sensor 105 can be achieved directly without carrying out a Fourier transformation.

In order to compare frequency characteristics, measurements were carried out as in the eighth embodiment using a miniature single-resonance type acoustic-emission sensor (Physical Acoustics Company; product name PICO) and a wide-band non-resonance type acoustic-emission sensor (produced by Fuji Ceramics Company; calibration reference instrument REF10M; frequency band 0–10 MHz), both available on the market. The same measurements were carried out as in the case of the acoustic-emission sensor 105.

Figure 25:
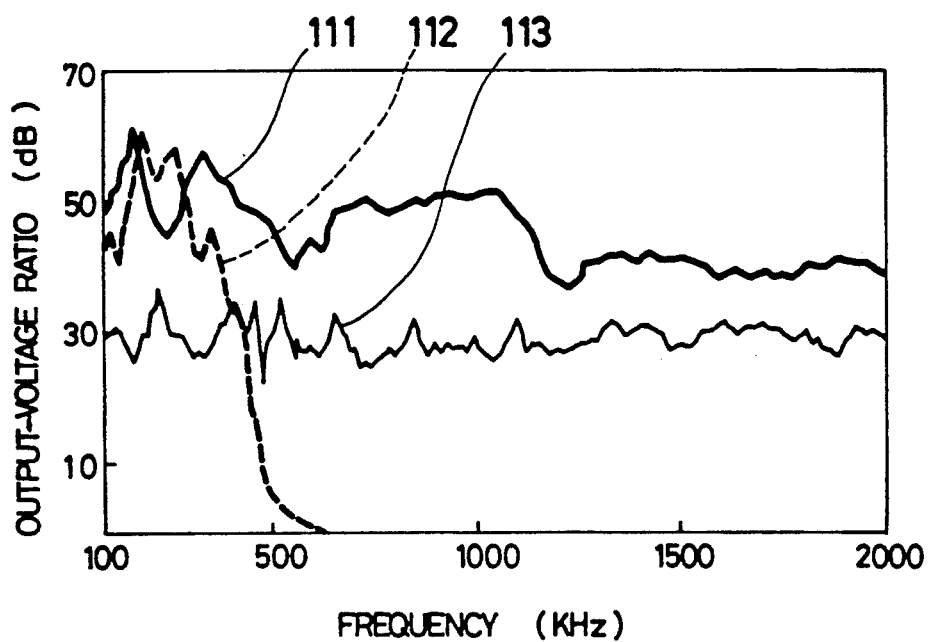

FIG. 25 shows the measurement results. A longitudinal axis is an output-voltage ratio of a detected signal of the acoustic-emission sensor 105. A transverse axis is the frequency. A reference output voltage is achieved by measuring an output voltage after replacing the acoustic-emission sensor 105, which receives signals (see FIG. 24), with a sensor identical to the sound-source sensor 108.

A curve line 111 shows a frequency spectrum of the resonance-dispersion type acoustic-emission sensor 105 of the present embodiment which has the metal housing 106 (FIG. 23). The curved lines 112 and 113 respectively show frequency spectra of the miniature single-resonance type acoustic-emission sensor and the wide-band non-resonance type acoustic-emission sensor.

Comparing the curved lines 111 and 112 it is clear that the acoustic-emission sensor 105 of the present embodiment has a much wider band than the miniature single-resonance type acoustic-emission sensor and has the same degree of high sensitivity.

Comparing the curved lines 111 and 113 it is clear that the acoustic-emission sensor 105 of the present embodiment exceeds the sensitivity of the wide-band non-resonance type acoustic-emission sensor by 10–20 dB and has an equally wide range.

As described above, the acoustic-emission sensor 105 of the present embodiment can be used for qualitative analysis to detect any damage that occurs inside a test material since the detecting frequency band is wide. Moreover, the acoustic-emission sensor 105 can also be used for quantitative analysis to detect stages of progression of the damage, since the acoustic-emission sensor 105 preferentially detects the longitudinal oscillation mode from among the acoustic-emission waves. Furthermore, the acoustic-emission sensor 105 is miniature-sized and has a high detection sensitivity since the composite synthetic resin-ceramic piezoelectric element 91, which has superior piezoelectric properties, is used.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An acoustic-emission sensor comprising:
    a receiving plate for receiving acoustic-emission waves; and
    a composite synthetic resin-ceramic piezoelectric element for converting the acoustic-emission waves received by the receiving plate into electric signals, wherein the composite synthetic resin-ceramic piezoelectric element includes
        a plurality of columnar ceramic piezoelectric bodies disposed in a synthetic-resin matrix, each columnar ceramic piezoelectric body polarized in a longitudinal direction, each columnar ceramic body arranged substantially mutually parallel to each other, and first and second electrodes being provided at respective ends of said columnar ceramic piezoelectric bodies and the receiving plate being fixed to said first electrode, wherein a weight for pressing down the composite synthetic resin-ceramic piezoelectric element on the receiving plate is attached to said second of the electrodes, the second electrode being opposite to the first electrode whereon the receiving plate is fixed.

2. An acoustic-emission sensor comprising:

a receiving plate for receiving acoustic-emission waves; and a composite synthetic resin-ceramic piezoelectric element for converting the acoustic-emission waves received by the receiving plate into electric signals, wherein the composite synthetic resin-ceramic piezoelectric element includes a plurality of columnar ceramic piezoelectric bodies disposed in a synthetic-resin matrix, each columnar ceramic piezoelectric body polarized in a longitudinal direction, each columnar ceramic body arranged substantially mutually parallel to each other, and first and second electrodes being provided at respective ends of said columnar ceramic piezoelectric bodies and the receiving plate being fixed to said first electrode, wherein the columnar ceramic piezoelectric bodies have inclined faces on upper parts thereof.

3. An acoustic-emission sensor comprising:

a receiving plate for receiving acoustic-emission waves; and a composite synthetic resin-ceramic piezoelectric element for converting the acoustic-emission waves received by the receiving plate into electric signals, wherein the composite synthetic resin-ceramic piezoelectric element includes a plurality of columnar ceramic piezoelectric bodies disposed in a synthetic-resin matrix, each columnar ceramic piezoelectric body polarized in a longitudinal direction, each columnar ceramic body arranged substantially mutually parallel to each other, and first and second electrodes being provided at respective ends of said columnar ceramic piezoelectric bodies and the receiving plate being fixed to said first electrode, wherein the columnar ceramic piezoelectric bodies have at least two different heights in a longitudinal direction.

4. An acoustic-emission sensor comprising:

a receiving plate for receiving acoustic-emission waves; and a composite synthetic resin-ceramic piezoelectric element for converting the acoustic-emission waves received by the receiving plate into electric signals, wherein the composite synthetic resin-ceramic piezoelectric element includes a plurality of columnar ceramic piezoelectric bodies disposed in a synthetic-resin matrix, each columnar ceramic piezoelectric body polarized in a longitudinal direction, each columnar ceramic body arranged substantially mutually parallel to each other, and first and second electrodes being provided at respective ends of said columnar ceramic piezoelectric bodies and the receiving plate being fixed to said first electrode, wherein the columnar ceramic piezoelectric bodies are circular-columnar in shape, wherein the columnar ceramic piezoelectric bodies are disposed concentrically in the synthetic-resin matrix, and wherein the columnar ceramic piezoelectric bodies have at least two different heights in a longitudinal direction.

5. The acoustic-emission sensor as set forth in claim 4, wherein the heights in a longitudinal direction of the columnar ceramic piezoelectric bodies which form a circle are substantially identical.

6. The acoustic-emission sensor as set forth in claim 5, wherein a side-face electrode is provided on a side face of the composite synthetic resin-ceramic piezoelectric element, the side-face electrode being connected to the one of the electrodes whereon the receiving plate is fixed.

7. The acoustic-emission sensor as set forth in claim 6, wherein a metal case is provided above the receiving plate for housing the composite synthetic resin-ceramic piezoelectric element.

8. An acoustic-emission sensor comprising:

a receiving plate for receiving acoustic-emission waves; and a composite synthetic resin-ceramic piezoelectric element for converting the acoustic-emission waves received by the receiving plate into electric signals, wherein the composite synthetic resin-ceramic piezoelectric element includes a plurality of columnar ceramic piezoelectric bodies disposed in a synthetic-resin matrix, each columnar ceramic piezoelectric body polarized in a longitudinal direction, each columnar ceramic body arranged substantially mutually parallel to each other, and first and second electrodes being provided at respective ends of said columnar ceramic piezoelectric bodies and the receiving plate being fixed to said first electrode, wherein the composite synthetic resin-ceramic piezoelectric element is circular-columnar and is oriented so that an axis thereof is parallel to the longitudinal direction, a metal ring being fixed on the circular-columnar composite synthetic resin-ceramic piezoelectric element to be connected to a side-face electrode which is provided on a side-face thereof so that the side-face electrode is connected to the one of the electrodes whereon the receiving plate is fixed.

* * * * *